United States Patent
Tobey, Jr. et al.

(10) Patent No.: US 6,325,934 B1
(45) Date of Patent: Dec. 4, 2001

(54) ENZYME AND BACTERIAL COMBINATION IN A SLOWLY DISSOLVABLE MATRIX FOR SEPTIC TANKS, GREASE TRAPS AND WASTE TREATMENT

(76) Inventors: James Francis Tobey, Jr., 2155 Stonemill Dr., Salem, VA (US) 24153; Raymond D. Stapleton, Jr., 132 Woodland Dr., Staunton, VA (US) 24401

( * ) Notice: Subject to any disclaimer, the term of this patent is extended or adjusted under 35 U.S.C. 154(b) by 0 days.

(21) Appl. No.: 09/567,152

(22) Filed: May 9, 2000

(51) Int. Cl.[7] .............................. C02F 3/00; C12N 11/08
(52) U.S. Cl. ...................... 210/606; 210/611; 210/616; 210/631; 210/632; 435/177; 435/180; 435/182
(58) Field of Search ..................... 210/606, 610, 210/611, 615, 616, 631, 632, 532.2; 435/174, 176, 177, 180, 182

(56) References Cited

U.S. PATENT DOCUMENTS

| | | |
|---|---|---|
| 3,242,055 | 3/1966 | De Lucia . |
| 3,791,927 * | 2/1974 | Forgione et al. . |
| 4,250,267 * | 2/1981 | Hartdegen et al. . |
| 4,810,385 * | 3/1989 | Hater et al. . |
| 5,089,407 | 2/1992 | Baker et al. . |
| 5,275,943 | 1/1994 | DiTuro . |
| 5,543,309 | 8/1996 | Pischel . |
| 5,580,770 * | 12/1996 | DeFilippi . |
| 5,719,115 | 2/1998 | Paatz et al. . |
| 5,905,037 | 5/1999 | Cooney et al. . |

* cited by examiner

Primary Examiner—David A. Simmons
Assistant Examiner—Fred Prince
(74) Attorney, Agent, or Firm—Donovan Lee Favre (57) ABSTRACT

Sewage waste digestive bacteria and enzymes are incorporated into a slow release material and delivered to the site of the waste to digest the solid waste. The slow release material is made heavy so the enzymes and bacteria will be delivered to the sludge in the bottom of a sewage digester chamber and made fat soluble so that the enzymes and bacteria will be delivered to the grease in the waste system to be digested. This selective delivery system prevents the enzymes and bacteria from being diluted in grey water rendering them less effective and discharged from the sewage system without digesting waste.

48 Claims, 2 Drawing Sheets

ENZYME AND BACTERIAL COMBINATION IN A SLOWLY DISSOLVABLE MATRIX FOR SEPTIC TANKS, GREASE TRAPS AND WASTE TREATMENT

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF INVENTION

1. Field of the Invention

This invention relates to granules of a slowly dissolving, water soluble. thermoplastic matrix containing enzymes, bacteria or bacteria/enzyme combinations, and to their use in granular septic tank bioaugmentation preparations, grease trap cleaning formulations and other bioremediation agents.

2. Discussion of the Related Art

Septic tanks and other biological treatment devices and facilities stabilize influent waste by removing biochemical oxygen demand (BOD), mineralizing carbon-containing compounds, digesting organic solids, and converting other compounds to chemical forms that are less damaging to the environment. It is important that organic components that might occlude, accumulate, and coat waste treatment, waste holding and waste conveying systems be dissolved and digested in an environmentally acceptable manner. Enzymes, bacteria, and bacteria-containing enzyme rearations are widely used in septic tank treatments, bioaugmentation agents, grease trap treatments, and bioremediation for other biological waste water processes. There is also a problem of sludge accumulation in lagoons and pits designed for the digestion of human and animal waste which needs a solution. Normally the granulated bacteria and enzymes are used as components of a comprehensive or diverse formulation which contains active ingredients compounded to enhance and accelerate the digestion of waste products. Preparations of this type are known as bioaugmenitation or bioenhancement agents. The three types of biological components of a bioenhancement agent, that is enzymes, bacteria or bacteria/enzyme combinations may be used in varying concentrations depending upon the situation. For example, some geographic areas regulate products in such manner that only viable bacteria containing additives may be used; free, active enzymes must be excluded from bioaugmentation products. In other areas combination products are used. Additionally, situations that are in food processing or medical facilities may require enzyme only (bacteria-free) products for waste treatment.

Enzymatic components and bacterial components of comprehensive formulations and enzyme/bacteria culture combinations have been used extensively to provide digestive activity in such situations. For example, previous U.S. Pat. No. 5,905,037 (Cooney—Tobey of the present invention, et al.) (May 18, 1999) describes the process and composition containing a cellulase and other enzymes with bacteria which accelerate the fiber digestion and removal of solids from septic tanks and cess pools. The U.S. Pat. No. 5,905, 037 discusses Cellulases, Lipases, Proteases, Amylases and the bacteria that generate such enzymes at column 4, line 62 to column 7 line 48. which discussion is hereby incorporated by reference.

In order to maintain continuous activity of supplemental bioenhancing ingredients such as the aforementioned bacteria and enzymes, conventional art teaches the continual addition either by manual or mechanical timed addition of bioaugmentation agents to a waste water treatment, holding or conveying system. Some products specify hourly, daily, or weekly additions to waste-containing containing systems. The need for this continual addition is to maintain incremental and continuous levels of activity from the enzymes, bacteria and other biologically active components so as to have more effect upon treatment efficiency. The mechanical addition is often expensive and maintenance intensive. Manual addition is traditionally unreliable.

Other related patents include:

U.S. Pat. No. 3,242,055 DeLucia (Mar. 22, 1966) discloses at column 3, lines 1–16, "As is shown in FIG. 2. the pellet 35 comprises a blend of powder or crystalline type enzyme material 35A, e.g. lipase, trypsin, amylase, pepsin or the like, and metal filings 35B that are bonded together by a suitable bonding agent, ie. animal glue, animal glue mixed with skimmed milk, casein glue, or any suitable water soluble glue or binder non-reactive to the enzymes. The pellets 35 are sized and shaped so that they can be readily passed through the soil pipes leading to tank 20. The purpose of the metal filings, e.g. iron filings, is to weight the pellets 35. Thus as pellet 35 is introduced into the tank, it will immediately sink to the bottom of the tank and come to rest in direct contact with the sludge 30 where active bacterial action is most desired. DeLucia does not address cellulases.

At column 3. lines 43–48 it is disclosed, "If desired, such enzyme pellet construction can be sold and distributed in package containing a number of pellets bonded with each of the bonding agents above described. Trhus immediate and long lasting bacterial action can be attained by depositing one or more of the differently bonded pellets into the tank."

In FIG. 1, one pellet 35 is shown in the septic tank.

The enzyme activity of DeLucia will be concentrated around the one or limited number of pellets added to the tank.

U.S. Pat. No. 5,275,943 DiTuro (Jan. 4, 1994) discloses at the abstract, "Tablets are formed that release components over time for biological degradation of organic matter such as sewage sludge, petroleum hydrocarbons, pesticides and herbicides. The tablets contain an inner-core of a dormant live microorganism, an inner-coating over the inner-core of water soluble hydroxypropyl methylcellulose or polypropylene glycol, an outer-layer over the inner coating of sodium sulfate coated sodium carbonate peroxyhdrate particles, and an outer-coating over the outer-layer of water soluble hydroxypropyl methylcellulose or polyethylene glycol. The inner core may contain a binder such as paraffin, gelatin and dextrose, and the outer-layer may contain additives such as enzymes, buffering agents, sugars and manganese dioxide as an oxidation catalyst. When the tablets are placed in an aqueous environment, layers of the tablet dissolve over time releasing components therein." At Column 1, lines 7 through 14 DiTuro discloses "This invention is directed to a nontoxic in situ method for the accelerated biological degradation of organic matter in the form of sewage sludge or petroleum hydrocarbons on the surface of aquatic objects submerged in bodies of saltwater, brackish, or freshwater". At col. 3, lines 21–27 DiTuro discloses "This invention proposes an in situ approach to help remediate this problem.

Its approach is one in which the ability of naturally occurring and/or seeded microorganisms to break down these contaminants is enhanced by the timed release of oxygen gas, via chemical reaction, and chemical additives such as buffering agents and enzymes."

One disadvantage of the DiTuro system is that the flow of oxygen away from the sludge will create a water current carrying the enzyme away from the sludge.

U.S. Pat. No. 5,543,309 Pischel (Aug. 6, 1996) at the abstract discloses, "A carrier is prepared containing bacteria and/or enzymes for degrading sewage sludge. The carrier can be in the form of a gel containing coloring matter and optionally a deodorant, or in the form of a core for a roll of toilet tissue or roll of towels.—The tube is formed from at least two layers made from cellulose bonded together with a water soluble bonding agent. Enzymes and/or bacteria can be in a slurry of cellulose pulp used to make the core, in the bonding agent, or in a coating or strip on an inside and/or outside layer. The tube contains a plurality of sets of circumferential perforations that enable, after removing the toilet tissue, readily breaking the tube into a plurality of small pieces that can be flushed down a toilet bowl into a sewage system where the pieces disintegrate and release the enzymes and/or bacteria.—"

U.S. Pat. No. 5,089,407 Baker et al (Feb. 18, 1992) discloses at the abstract, "Biological materials such as enzymes. proteins and peptides are encapsulated by forming a mixture of the material and an aqueous non-ionic polymer solution, spraying the mixture into a circulating water-immiscible non-solvent for the polymer at a temperature sufficient to freeze the beads and drying the frozen beads to remove—water—. Suitable non-ionic polymers are poly (vinyl alcohol), polyvinylpyrollidone, dextran and derivatized cellulose. A densification agent—may be present—. Encapsulated material such as microbes produced by this process provide useful agricultural agents —suitable for delivery to soil or plant leaves." At col. 2, lines 1 8–20 Baker et al disclose, "Water soluble non-ionic polymers having a solubility of at least 3% w/v and which are not detrimental to the microbe to be encapsulated can by used."

Except for DeLucia, the bacteria and/or enzymes normally added to a sewage digester tank are added as liquids or solids that immediately dissolve and flow into the digester tank, and many of the bacteria and/or enzymes continue to flow through the digester tank to the discharge without ever coming in contact with the sludge to be digested. DeLucia discloses adding a pellet or a number of pellets having different dissolution rates containing enzymes but no bacteria.

BRIEF SUMMARY OF THE INVENTION

The present invention relates to small granules of a slow release digesting composition which, in one embodiment, preferably sinks and is distributed to the entire bottom area of the digester to digest the sludge. In another embodiment, the granules are grease soluble and digest grease. Another embodiment, combines the two. The digesting composition of the present invention is preferably made by incorporating bacteria/enzyme combinations and other biologically active materials in a matrix in order to create a time sustained release of biologically active components including viable bacteria, enzymes, and other beneficial compounds such as nutrients into an aqueous waste environment. Instead of the combination, bacteria, or enzymes can be incorporated into the matrix separately, but this is not preferred. The enzymes initiate the digestion of the sludge and are active only for a day to a week depending upon the formulation, whereas the bacteria become a permanent digestive colony. The purpose of said invention is to render the active components efficiency in a waste water treatment, holding or conveying systems more economical and trouble-free.

The composition of the present invention is made by heating a surfactant having a softening or melting point of from 30 degrees Celsius to 100 degrees Celsius to its softening point, adding the bacteria/enzyme combination and other ingredients then converting the product to small granules which can be flushed down a toilet. The surfactant can be present at a level of from 1% to 50% or more of the total composition.

To be more specific the present invention is directed to a dry granulated composition for the treatment of sewage sludge in the bottom of a sewage digestion chamber. The composition comprises saprophytic waste degrading bacteria and hydrolytic waste degrading enzymes dispersed in a slow release material which slowly and continuously releases the majority of the bacteria and enzymes over a period of a day to a week in water. The composition preferably has a density greater than water whereby when the composition is added to the sewage digestion chamber, the composition sinks and releases the bacteria and enzymes to digest the sludge in the bottom of the digestion chamber. The composition is free of substantial amounts of oxygen generating compounds which would cause an upward flow of water in the digestion chamber and carry the bacteria and hydrolytic enzymes upward and away from the sludge.

The slow release material is preferably a material with limited and controlled water solubility which slowly and continuously releases the bacteria and hydrolytic enzymes over a period of a day to two weeks or more. The slow release material is preferably a surfactant with specific characteristics. The surfactant is preferably a polyether having a melting point between thirty degrees Celsius and one hundred degrees Celsius which will allow the surfactant to remain a solid in use and allow the incorporation of the bacteria and hydrolytic enzymes into the surfactant by mixing without high temperature degradation of the bacteria and hydrolytic enzymes. Bacteria and enzymes can withstand high temperature for a short period of time in the absence of moisture or water.

The composition is preferably non oxygen generating and preferably does not generate any large quantities of other gases which would cause a water current upward to carry the bacteria and hydrolytic enzyme away from the sludge it was designed to digest.

The granulated composition of the present invention is comprised of granules containing the bacteria and hydrolytic enzymes. The bacteria and/or hydrolytic enzymes preparation is dispersed homogeneously in a matrix composed of 10% to 50% by weight based upon the weight of the total composition, of an organic surfactant soluble in water over a period of one day to two weeks. That is to say that the surfactant is sufficiently soluble in water to release the majority of the contained bacteria and hydrolytic enzyme over a period of one day to two weeks. A surfactant can be selected that is also preferably soluble in triglyceride fats and oils, and/or mineral oil. And two different granulated compositions can be employed, one composition containing a surfactant which is relatively more soluble in fats than the other. In this way the bacteria and hydrolytic enzyme can be delivered directly to the fat and grease it was designed to digest and not be diluted and flushed away in the water phase, in addition to treating the sludge layer. To increase the fat solubility of the polyether, more hydrocarbon is added to an end of the polyether to make the end more non polar and hence more fat soluble. For example and end containing six or more carbon atoms in a hydrocarbon chain or ring. Along the same lines, enzymes and/or bacteria not in a matrix can be added to the granulated composition to speed up the initial digestion of the sewage then pass through the digester tank leaving the granulated composition to provide long term digestion.

To further control the rate of release of the bacteria and hydrolytic enzyme said surfactant is preferably combined with a non-toxic wax. This also increases the fat solubility of the granulated composition. The wax can be selected from the class comprising paraffin wax, wax of natural orgin such as beeswax or synthetic wax. The preferred wax is a paraffin wax. Paraffin wax is a hydrocabon or petroleum wax. The wax is preferably present in range of 1% to 50% of the weight of the total composition.

The bacteria and hydrolytic enzymes used for incorporation into the matrix are initially absorbed onto a base which is an absorbant component, preferably an organic, biodegradable component prior to being incorporated into the slowly water soluble matrix. The organic absorbent base is preferably wheat bran.

The bacteria are chosen from a group of genera and species that produce hydrolytic enzymes.

In one embodiment the bacteria are composed of one or more strains selected from a group comprised of grease digesting bacteria. The preferred grease digesting bacteria are composed of one or more strains selected from the genus Bacillus, Pseudomonas or Cellulomnonas. Also preferred are bacteria composed of one or more strains selected from a group comprised of *Pseudomonas putidca*, and *Pseudomonas oleovorens*. The grease digesting bacteria and/or the grease digesting enzymes, amylase and lipase are preferably incorporated into a fat or grease soluble matrix.

Also preferred are bacteria selected from the spore-forming Bacillus genus including one or more strains selected from a group comprised of *Bacillus subtilis, Bacillus lichenifornmis, Bacillus amyloliquefaciens Paenibacillus polymyxa, Bacillus megaterium, Bacillus psychrophilus, Bacillus globiformis, Bacillus psychrosaccharolyticus, Bacillus benzoevorans, Bacillus vallismortis, Bacillus mojavensis, Bacillus stearothermophilus*, and *Bacillus acidopullyticus*.

Also preferred are bacteria selected from a group of psychrophillic bacteria which survive and grow well at temperatures in the range of 0° C. to 20° C. including but not limited to the group comprising *Bacillus psychrosaccharolyticus, Bacillus psychrophilus, Bacillus macqaerians, Bacilllus cerers, Bacillus globisporus*, and *Paenibacillus macquariensis*.

The grease digestive bacteria are preferably contained in a matrix of slow release material soluble in triglyceride fats and oils, and/or mineral oil. The slow release material is preferably a surfactant combined with a non-toxic wax. The said wax is preferably present in range of 1% to 50% by weight of the total composition.

The bacteria containing granules of the present invention arc comprised of saprophytic waste degrading viable bacteria and/or bacteria spores dispersed in a surfactant. The surfactant is present in an amount of from 1% to 99% based upon the weight of the total composition. A major portion of the surfactant is soluble in 20 degree Celsius water over a period of from one to fourteen days. Prior to their dispersal into the surfactant matrix, the bacteria and/or spores are preferably absorbed onto or immobilized on a base which preferably is an organic, biodegradable component. The organic granule base is preferably wheat bran. The bacteria are chosen from a group of genera and species that produce hydrolytic enzymes.

In another embodiment the present invention is directed to enzyme granules which sink to the bottom of a digester tank to digest the sludge which settles at the bottom. These granules contain enzyme dispersed in from 1% to 80% by weight based on the total weight of the granules of an organic surfactant of limited solubility in water, and contain a sufficient amount of a relatively high density material suitable for inclusion in biological waste treatment, waste holding and waste conveying systems to increase the rate at which the granules to sink in water. The high density material is preferably selected from the group comprising calcium carbonate, magnesium carbonate sodium bicarbonate ground marble that is most preferably limestone, which is customarily composed of calcium carbonate or calcium carbonate and magnesium carbonate in natural form. The high density material also preferably helps to control the pH and also helps to stabilize enzymes. For this later purpose the high density material is selected from a group of carbonic salts which are pH regulating substances suitable for inclusion in biological waste treatment, waste holding and waste conveying systems. The high density material also preferably dissolves at it neutalizes the acid waste. Because of this feature the high density material does not accumulate in the digester tank, and it is not composed of any hazardous metal which could accumulate in the soil or groundwater or clog a drain field.

In another embodiment the present invention is also directed to a method of treating sewage in a digestion chamber to digest the sludge in the bottom of the digestion chamber. The method comprises adding to the digestion chamber granules of a composition comprising bacteria and enzymes in slow release material which slowly releases the majority of the bacteria and enzymes over a period of a day to two weeks in water. The composition has a having a density greater than water whereby when the composition is added to the digestion chamber the composition sinks and releases the bacteria and enzymes to digest the sludge in the bottom of the digestion chamber. The slow release material is preferably a slowly water soluble matrix. The slow release material is preferably a surfactant. The surfactant is preferably a polyether having a melting point between thirty degrees Celsius and one hundred degrees Celsius. The high density granules can be combined with grease soluble granules of lesser density containing grease digesting enzymes and/or grease digesting bacteria.

It is preferred that none of the components in the granules generate sufficient oxygen to carry the digestive enzymes and bacteria from the sludge.

The method of the present invention can also be employed for treating a lagoon or pit containing human or animal waste to digest the sludge in the bottom of the lagoon or pit. Again the invention comprises adding to the lagoon or pit granules of a composition comprising bacteria and enzymes in slow release material which slowly releases the majority of the bacteria and enzymes over a period of a day to a week in water. The composition has a having a density greater than water so that when the composition is added to the lagoon or pit, the composition sinks and releases the bacteria and enzymes to digest the sludge in the bottom of the lagoon or pit. The composition is non-oxygen releasing to prevent a flow of the digesting bacteria and enzymes away from the sludge. The slow release material is preferably a water soluble matrix surrounding the bacteria and enzymes. The slow release material is preferably a surfactant. The surfactant is preferably a polyether having a melting point between thirty degrees Celsius and eighty degrees Celsius.

The terms "digestion tank" and "digestion chamber" include septic tanks, cesspools and tanks and chambers in sewage disposal plants. The invention is also useful is treating waste lagoons.

When the disposal system is anaerobic, the bacteria used are preferably bacteria with activity under anaerobic conditions.

The slow release material which forms the matrix in the present invention is preferably a polyether having a melting or pour point of from 30 degrees Celsius to 100 degrees Celsius. Such polyethers are commercially available under the Trademarks: Sipol CSA-20, Sipol CSA-30 (Harcros); Eumulgin B-1. Eumulgin B-2, Eumulgin B-3, Generol N 122 E-5, Generol N 122 E-10 (Henkel), T-Det XH, T-Det BP-1 and T-Det EPO-104. These include polyalkylene glycol ether, stearyl alcohol ethoxylated with from about 5 to 10 moles of ethylene oxide, and cetyl alcohol ethoxylated with from 10 to 30 moles of ethylene oxide.

The composition of the present invention can be introduced into a digestion chamber by flushing the composition down the toilet or drain. The composition can be introduced into grease traps and sewage conduits by flushing down a drain, or metering into an influent flow. The composition of the present invention can also be broadcast over the surface of a lagoon, pit or chamber.

The section of U.S. Pat. No. 5,905,037 which is incorporated by reference into the present application discloses the various enzymes that can be employed in the present invention. These include cellulases, lipases. proteases, and amylases. The Patent also discloses bacterial systems that can be employed in the practice of the present invention.

The preferred final granulated product has an average diameter of 0.5 to 5 mm and preferably 1 to 2.5 mm. The proportions of ingredients are not critical so long as there is a small but sufficient amount of slowly water soluble matrix to surround each enzyme and each bacteria to provide the required timed release.

In one embodiment the product is made by heating a polyether having a softening point of from 30 degrees Celsius to 100 degrees Celsius to or above the softening point of the polyether, adding to the softened polyether, saprophytic waste degrading viable or dormant bacteria and/or one or more waste degrading hydrolytic enzymes, mixing the polyether and the bacteria and/or enzymes to form a uniform dispersion, then granulating the dispersion to granules having, an average thickness of from 0.5 to 5.0 mm.

DETAILED DESCRIPTION OF THE INVENTION

Figure 1:
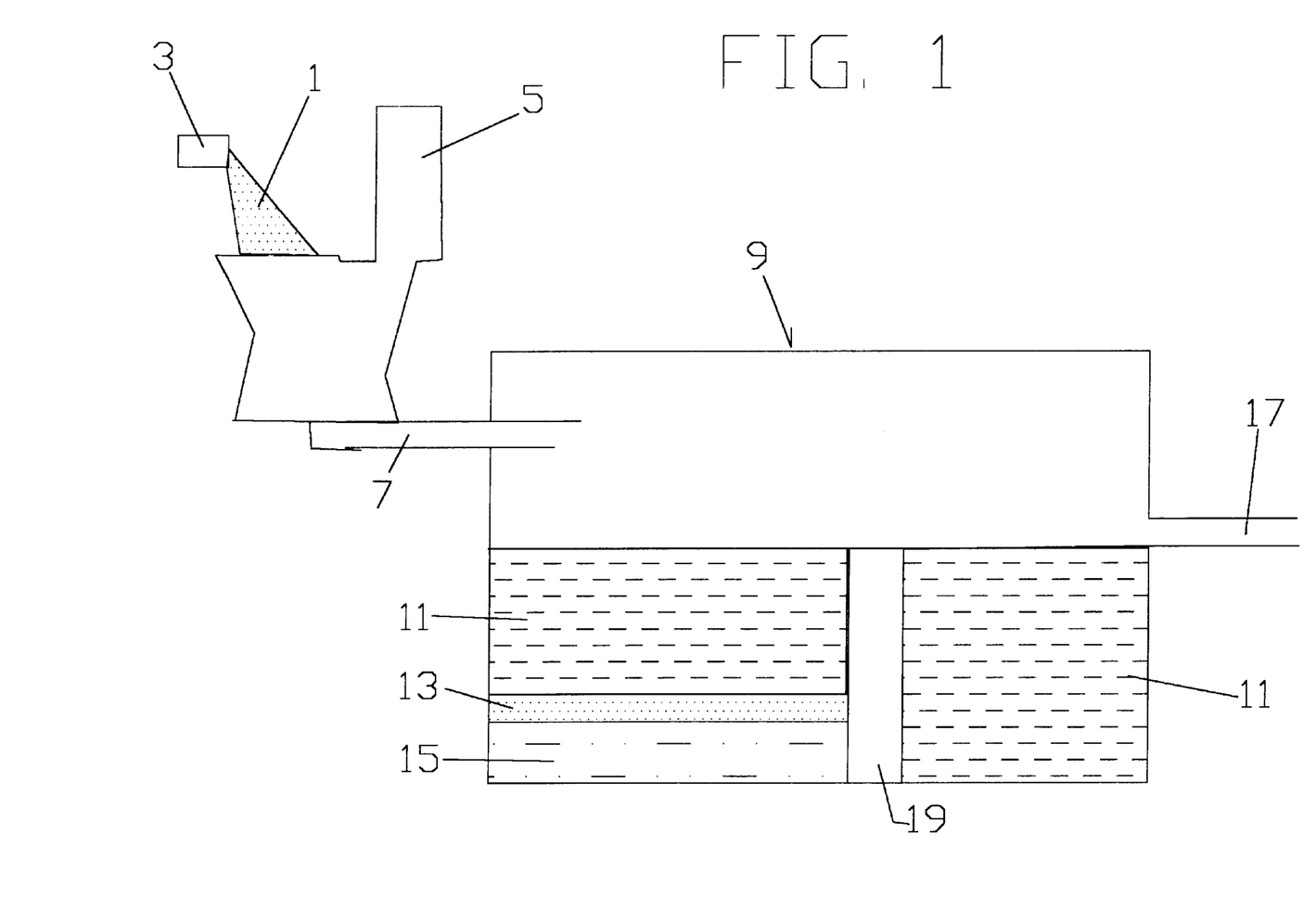
FIG. 1 shows how the slow release granules of the present invention are introduced into a septic tank through a toilet.
Figure 2:
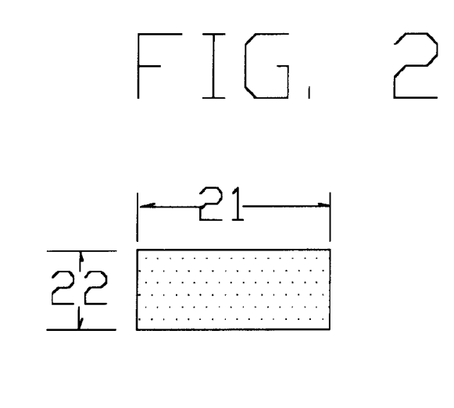
FIG. 2 is a top view of a granule of the present invention showing how the diameter or thickness of the granule is measured.
Figure 3:
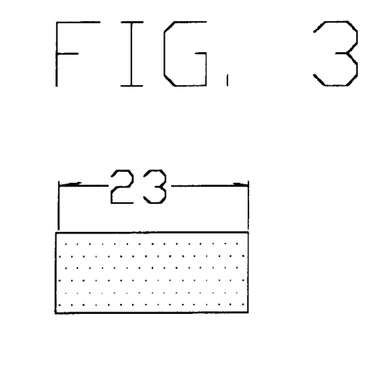
FIG. 3 is a side view of a granule of the present invention showing how the diameter or thickness of the granule is measured.
Figure 4:
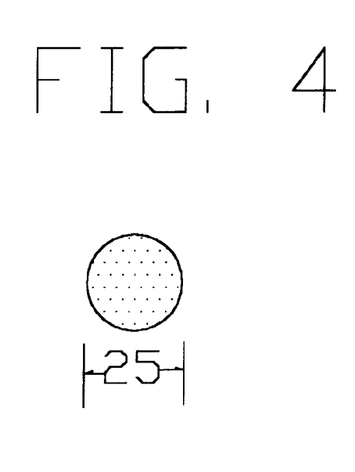
FIG. 4 is an end view of a granule of the present invention showing how the diameter or thickness of the granule is measured.

Turning now to FIG. 1, there is shown the granules 1 of the present invention being introduced from a box 3 into a toilet 5. Flushing toilet 5 carries granules 1 through drain pipe 7 into septic tank 9. The granules 1 settle through grey water 11 dispersing uniformly across the top 13 of sludge layer 15. The granules 1 will sink into sludge layer 15 with time. The grey water exits the septic tank 9 through discharge line 17 after passing barrier 19. In FIG. 2, FIG. 3 and FIG. 4, the diameter or thickness of the granule is depicted by the reference numerals 21, 22, 23 and 25. ache terms "diameter" and "thickness" are used interchangeably, and are not critical. All that is required is that the granules be able to pass through the toilet 5 and uniformly disperse in sludge layer 15.

The following examples provide instructions for preparing the granules. The same surfactant was used throughout all of the examples.

EXAMPLE 1

A dry, granulated enzyme preparation was prepared using the following ingredients:

| Ingredient | Percent by weight |
| --- | --- |
| Cellulase Enzyme on prilled titanium dioxide (Maxicel 150 ™ enzyme from George A Jeffreys & Co., Inc.) | 67 |
| Ethoxylated soy sterols Surfactant (melting point 80 degrees Celsius | 33 |

Upon liquefaction, the surfactant was physically blended (homogenized) with a mixer with the enzyme until a uniform consistency was achieved. The coating/enzyme was then allowed to cool and solidify at room temperature (approximately 26° C.). This allowed a uniform layer of surfactant to surround the enzyme. The composition can be formed into granules using a chopping extruder.

To break down grease, the cellulase is replaced with any amylase or lipase, product granulated and then used to liquify grease in grease traps. The ethoxylated (epoxidized) soy sterols are fat soluble due to the large non polar sterol end groups on the molecules. The enzyme is preferably present in a range of from 25% to 75% and the surfactant is also preferably present in a range of from 25% to 75% of the two ingredients.

Wax can be added to the composition to increase the grease solubility and to decrease the density. The density without the wax is greater than the density of water.

EXAMPLE 2

In many waste treatment lagoons, cesspools and septic tanks there is often a disproportionate amount of organic solids accumulation in the bottom (lower layers) of the liquid treatment area. It is desirable that this solid matter be effectively liquefied, suspended and hydrolytically degraded by enzymes and/or bacteria. Enzymes and/or bacterial bioaugmentative additives, when added to such waste treatment areas become suspended, dissolved, or solubilized in the upper, aqueous phase of the treatment area and may be diluted or washed from the system by normal hydraulic flow prior to their diffusion into the lower, more solid intensive layers or phases of the treatment area. This results in less application of hydrolytic activity to the organic solids in the bottom and impairs a product's performance in specific circumstances. We have found that if the previously described coating, and the active bacteria and/or enzyme components are linked to a granule with relatively high specific gravity (i.e. treater than that of water), then uniform delivery of the active bioaugmentative activity to the treatment area which has the greatest need is enhanced. The high-density granule (densifying agent) may be of various physical and chemical nature but must be non-toxic to both bacteria and/or enzymes used in the bioaugmentation product. The high density granule (densifying agent) should also be chosen from compounds which arc not damaging to the effluent quality.

A dry, granulated enzyme preparation in combination with a granulated dolomitic limestone densifying agent (partical size 0.5 mm to 5.0 mm) was developed using the following ingredients and procedure.

| Ingredient | Percent by weight |
|---|---|
| cellulase micro granules enzyme | 33 |
| limestone particles densifying agent | 33 |
| ethoxylated soy sterols surfactant (5 to 10 ethoxy units) (or ethoxylated cetyl alcohol 10–30 ethoxy units) surfactant | 34 |

Upon liquefaction, the surfactant was physically blended (homogenized) with a mixer or by hand with the enzyme and limestone granules until a uniform consistency was achieved. The coating/enzyme was then allowed to cool and solidify at room temperature (approximately 26° C.). This allowed a uniform layer of surfactant to surround the enzyme and limestone granules.

The preferred range of ingredients in percentage by weight based upon the three components are 10% to 70% enzyme, 10% to 70% densifying agent, and 10% to 70% of surfactant.

EXAMPLE 3

A dry, granulated enzyme preparation was developed using the following ingredients and procedure.

| Ingredient | Percent by weight |
|---|---|
| Cellulase Enzyme on prilled titanium dioxide (Maxicel 150 ™ enzyme) | 50 |
| Ethoxylated soy sterols Surfactant (melting point 80 degrees Celsius) | 25 |
| Paraffin Wax | 25 |

Upon liquefaction, the surfactant wax combination was physically blended (homogenized) with a mixer with the enzyme until a uniform consistency was achieved. The coating/enzyme combination was then allowed to cool and solidify at room temperature (approximately 26° C.). This allowed a uniform layer of surfactant to surround the enzyme granule. Upon granulation this composition is useful to break down animal fats in grease traps and sewer lines.

The preferred range of ingredients in percentage by weight based upon the three components are 10% to 70% enzyme, 10% to 70% wax, and 10% to 70% of surfactant.

EXAMPLE 4

A dry, granulated enzyme preparation in combination with a granulated limestone carrier (partical size 0.5 mm to 5.0 mm), enzyme, surfactant and wax was prepared using the following ingredients and procedures.

| Ingredient | Percent by weight |
|---|---|
| cellulase micro granules enzyme | 33 |
| limestone particles densifying agent 0.5 mm to 5 mm particle size | 33 |
| ethoxylated soy sterols surfactant (5 to 10 ethoxy units) | 17 |
| Paraffin Wax | 17 |

Upon liquefaction, the surfactant wax combination was physically blended (homogenized) with a mixer with the enzyme and limestone granules until a uniform consistency was achieved. The coating/enzyme and limestone was then allowed to cool and solidify at room temperature (approximately 26° C.). This allowed a uniform layer of surfactant to surround the enzyme and limestone granules.

The preferred range of ingredients in percentage by weight based upon the three components are 7.5% to 70% enzyme, 7.5% to 70% densifying agent, 7.5 to 70% wax and 7.5% to 70% of surfactant.

Example 4 was repeated replacing half of the enzyme with *Bacillus psychrohilus* on bran. The enzymes in all of the above Examples can be replaced in whole or in part with viable bacteria and/or bacteria spores. The BACKGROUND OF THE INVENTION lists large numbers of bacteria that can be employed.

Any enzyme can be used in any of the examples, alone or in combination with other enzymes as the method of the present invention prevents interreaction of the enzymes. In an aqueous media, the enzymes can react with each other.

The enzyme activity of the granules of the present invention over time were measured using the following procedure. Basically a specific amount of water is added to the granules, and then added water is recovered at particular time intervals at tested for enzyme activity. After a water sample is collected it is then replaced by a fresh water sample. More specifically:

1) Add 100 ml of water to 0.5 grams of granules.
2) Swirl in beaker for 15 seconds, then allow sample to settle for 15 minutes, collect water sample and add a fresh 100 ml of water.
3) Swirl for 15 seconds, then allow to settle until next tine point a day later.

By this method enzyme activity was determined to be extended to two weeks using the slow release polyether matrix of the present invention.

What is claimed is:

1. A dry granulated composition for the treatment of sewage sludge in the bottom of a sewage digestion chamber, the composition comprising saprophytic waste degrading viable or dormant bacteria and waste degrading hydrolytic enzymes dispersed in a slow release material which slowly and continuously releases the majority of the bacteria and enzymes over a period of a day to two weeks in water, the composition having a density greater than water whereby when the composition is added to the digestion chamber the composition sinks, disperses in the sludge, and releases the bacteria and enzymes to digest the sludge in the bottom of the digestion chamber, the composition being free of substantial amounts of oxygen generating compounds which would carry the bacteria and hydrolytic enzymes away from the sludge.

2. The composition of claim 1 wherein the slow release material is a water soluble matrix.

3. The composition of claim 1 wherein the slow release material is a surfactant.

4. The composition of claim 3 wherein the surfactant is a polyether having a melting point between thirty degrees Celsius and one hundred degrees Celsius, granules comprising the granulated composition have an average diameter of from 0.5 mm to 5 mm.

5. The composition of claim 1 wherein the composition is non oxygen generating and contains nutrients for bacteria.

6. The granulated composition of claim 1 comprised of granules containing the bacteria and hydrolytic enzyme, the bacteria and hydrolytic enzyme being dispersed in a matrix composed of 1% to 50% by weight, based upon the weight of the total composition, of an organic surfactant soluble in water over a period of one day to one week.

7. The composition of claim 6 where said surfactant is soluble in triglyceride fats and oils, and/or mineral oil.

8. The composition of claim 6 wherein said surfactant is combined with a non-toxic wax.

9. The composition of claim 8 wherein the wax is selected from the class comprising paraffin wax, natural waxes, synthetic waxes and beeswax.

10. The composition of claim 9 wherein the wax is a paraffin wax.

11. The composition of claim 8 where the said wax is present in range of 1% to 50% of the weight of the total composition.

12. The composition of claim I wherein the bacteria and hydrolytic enzymes are absorbed onto a base prior to being dispersed into the slow release material.

13. The composition of claim 12 wherein the bacteria and hydrolytic enzymes are absorbed onto a base which is an organic, biodegradable component.

14. The composition of claim 1 wherein the bacteria are chosen from a group of genera and species that produce hydrolytic enzymes.

15. The composition of claim 14 wherein the bacteria are composed of one or more strains selected from a group comprised of fat digesting degradative bacteria.

16. The composition of claim 15 wherein the bacteria are composed of one or more strains selected from the genus Pseudomonas or Cellulomonas.

17. The composition of claim 15 Wherein the bacteria are composed of one or more strains selected from a group comprised of *Pseudomonas putida,* and *Pseudomonas oleovorens.*

18. The composition of claim 14 wherein the bacteria are selected from the spore-forming Bacillus genus.

19. The composition of claim 18 wherein the component bacteria are composed of one or more strains selected from a group comprised of *Bacillus subtilis, Bacillus licheniformis, Bacillus amyloliquefaciens, Paenibacillus polymyxa, Bacillus megaterium, Bacillus psychrophilus, Bacillus globiformis, Bacillus psychrosaccharolyticus, Bacillus benzovorans, Bacillus vallimortis, Bacillus mojavensis, Bacillus stearothermophilus,* and *Bacillus acidopullyticus.*

20. The composition of claim 14 wherein the bacteria are selected from a group of psychrophillic bacteria which survive and grow well at temperatures in the range of 0° C. 20° C.

21. The composition of claim 20 wherein the bacteria are selected from the group consisting of *Bacillus psychrosaccharolyticus, Bacillus psychrophilusk, Bacillus globisporus Paenibacillus macquariensis,* and *Bacillus cereus.*

22. The composition of claim 14 wherein said slow release material is soluble in triglyceride fats and oils, and/or mineral oil.

23. The composition of claim 14 wherein said slow release material is a surfactant combined with a non-toxic wax.

24. The composition of claim 23 wherein the said wax is present in range of 1% to 50% by weight of the total composition.

25. Bacteria containing granules comprised of saprophytic waste degrading viable and/or dormant bacteria dispersed in a surfactant matrix, the surfactant being present in an amount of from 1% to 99% of combined weights of the bacteria and surfactant, a major portion of the surfactant matrix being soluble in 20 degree Celsius water over a period of from one day to two weeks.

26. The granules of claim 25 wherein the bacteria are absorbed onto or immobilized on a base prior to being incorporated into the matrix.

27. The granules of claim 25 wherein the base is an organic, biodegradable component.

28. The granules of claim 25 wherein the bacteria are chosen from a group of general and species that produce hydrolytic enzymes, the granules have an average diameter of 0.5 to 5 mm and the granules contain nutrients for the bacteria.

29. The granules of claim 28 wherein the bacteria are composed of one or more strains selected from a group comprised of fat digesting degradative bacteria.

30. The granules of claim 29 wherein the bacteria are composed of one or more strains selected from the genus Pseudomonas.

31. The granules of claim 30 wherein the bacteria are composed of one or more strains selected from a group comprised of *Pseudomonas putida,* and *Pseudomonas oleovorens.*

32. The granules of claim 25 wherein the bacteria are selected from the spore-forming Bacillus genus.

33. The granules of claim 32 wherein the bacteria are composed of one or more strains selected from a group comprised of *Bacillus subtilis, Bacillus licheniformis, Bacillus amyloliquefaciens, Paenibacillus polymyxa, Bacillus megaterium, Bacillus psychrophilus, Bacillus globiformis, Bacillus psychrosaccharolyticus, Bacillus benzoevorans, Bacillus vallismortis, Bacillus mojavensis, Bacillus stearothermophilus, Bacillus pumilus, Paenibacillus amylolyticus* and *Bacillus acidopullyticus.*

34. Enzyme granules containing enzyme dispersed in a matrix of from 1% to 80 % by weight based on the total weight of the granules of an organic surfactant soluble in water over a period of one day to two weeks, and containing a sufficient amount of a relatively high density material suitable for inclusion in biological waste treatment, waste holding and waste conveying systems to cause the granules to sink in water to digest sludge in a digester tank.

35. The composition of claim 34 wherein the high density material is selected from a group of inorganic nontoxic compounds, and the granules have an average diameter of from 0.5 to 5 mm.

36. The composition of claim 35 wherein the high density material is selected from the group comprising calcium carbonate, magnesium carbonate, and sodium bicarbonate.

37. The composition of claim 35 wherein the high density material is selected from a group of carbonic salts which are pH regulating substances suitable for inclusion in biological waste treatment, waste holding and waste conveying systems.

38. The composition of claim 35 wherein the high density material is granular limestone.

39. A method of treating sewage in a sewage digestion chamber to digest the sludge in the bottom of the digestion chamber comprising adding to the digestion chamber granules of a composition comprising bacteria and enzymes in slow release material which slowly releases the majority of the bacteria and enzymes over a period of a day to a week in water, the composition having a having a density greater than water whereby when the composition is added to the digestion chamber the composition sinks and releases the bacteria and enzymes to digest the sludge in the bottom of the digestion chamber.

40. The method of claim 39 wherein the slow release material forms a water soluble matrix.

41. The method of claim 39 wherein the slow release material is a surfactant.

42. The method of claim 41 wherein the surfactant is a polyether having a melting point between thirty degrees Celsius and one hundred degrees Celsius, and the granules have an average diameter of 0.5 to 5mm.

43. The method of claim 39 wherein the composition is non oxygen generating, and the granules contain nutrients for the bacteria.

44. A method of treating a lagoon or pit containing human or animal waste to digest the sludge in the bottom of the lagoon or pit comprising adding to the lagoon or pit granules of a composition comprising bacteria and enzymes in slow release material which slowly releases the majority of the bacteria and enzymes over a period of a day to a week in water, the composition having a having a density greater than water whereby when the composition is added to the lagoon or pit the composition sinks and releases the bacteria and enzymes to digest the sludge in the bottom of the lagoon or pit, the composition being non-oxygen releasing.

45. The method of claim 44 wherein the slow release material is a water soluble matrix, and the granules have an average diameter of from 0.5 to 5 mm.

46. The method of claim 45 wherein the slow release material is a surfactant and contains nutrients for bacteria.

47. The method of claim 46 wherein the surfactant has a melting point between thirty degrees Celsius and one hundred degrees Celsius.

48. A method of making a composition for the treatment of waste in aqueous environment comprising heating a polyether having a softening point of from 30 degrees Celsius to 100 degrees Celsius to or above the softening point of the polyether, adding to the softened polyether saprophytic waste degrading viable or dormant bacteria and/or one or more waste degrading hydrolytic enzymes, mixing the polyether and the bacteria and/or enzymes to form a uniform dispersion, then granulating the dispersion to granules having, an average thickness of from 0.5 to 5.0 mm.

* * * * *

UNITED STATES PATENT AND TRADEMARK OFFICE
CERTIFICATE OF CORRECTION

PATENT NO. : 6,325,934 B1
DATED : December 4, 2001
INVENTOR(S) : Tobey et al.

It is certified that error appears in the above-identified patent and that said Letters Patent is hereby corrected as shown below:

Column 1,
Lines 36 and 37, "rearations" should read -- preparations --.
Lines 46 and 47, "bioaugmenitation" should read -- bioaugmentation --.

Column 2,
Line 2, "48." should read -- 48, --
Line 10, "containing" second occurrence should be deleted.
Line 37, "Trhus" should read -- Thus --.

Column 3,
Line 26, "enzymes. proteins" should read -- enzymes, proteins --

Column 5,
Line 14, "orgin" should read -- origin --.
Line 16, "hydrocabon" should read -- hydrocarbon --.
Line 21, "absorbant" should read -- absorbent --.

Column 6,
Lines 39 and 61, "having a" should be deleted.

Column 7,
Line 32, "lipases. proteases" should read -- lipases, proteases --.

Column 8,
Line 8, "ache" should read -- The --.

Column 9,
Lines 12 and 67, "partical" should read -- particle --.

Column 10,
Line 47, "tine" should read -- time --.

UNITED STATES PATENT AND TRADEMARK OFFICE
CERTIFICATE OF CORRECTION

PATENT NO. : 6,325,934 B1
DATED : December 4, 2001
INVENTOR(S) : Tobey et al.

It is certified that error appears in the above-identified patent and that said Letters Patent is hereby corrected as shown below:

Column 12,
Line 23, "general" should read -- genera --.

Column 14,
Line 26, "having," should read -- having --.

Signed and Sealed this

Second Day of December, 2003

JAMES E. ROGAN
*Director of the United States Patent and Trademark Office*